United States Patent
Hutchinson et al.

(10) Patent No.: US 10,295,480 B2
(45) Date of Patent: May 21, 2019

(54) APPARATUSES AND METHODS FOR HIGH-PRECISION MEASUREMENT

(71) Applicant: The Boeing Company, Chicago, IL (US)

(72) Inventors: Michael C. Hutchinson, Kent, WA (US); Steven K. Brady, Renton, WA (US); William D. Meade, Seattle, WA (US); Thomas A. Maeder, Lake Forest Park, WA (US)

(73) Assignee: The Boeing Company, Chicago, IL (US)

( * ) Notice: Subject to any disclaimer, the term of this patent is extended or adjusted under 35 U.S.C. 154(b) by 403 days.

(21) Appl. No.: 15/087,579

(22) Filed: Mar. 31, 2016

(65) Prior Publication Data
US 2017/0284947 A1 Oct. 5, 2017

(51) Int. Cl.
G01N 23/04 (2018.01)
G01N 23/18 (2018.01)

(52) U.S. Cl.
CPC ............. *G01N 23/04* (2013.01); *G01N 23/18* (2013.01); *G01N 2223/401* (2013.01); *G01N 2223/645* (2013.01); *G01N 2223/646* (2013.01)

(58) Field of Classification Search
CPC ........... G01N 2223/419; G01N 23/046; G01N 2223/046; G01N 2223/639; G01N 23/10; A61B 6/032
See application file for complete search history.

(56) References Cited

U.S. PATENT DOCUMENTS

| 6,003,237 A | 3/1999 | Sarr et al. |
| 8,899,113 B2 | 12/2014 | Fetzer et al. |
| 2012/0004513 A1* | 1/2012 | Robinson ............. G01T 1/2985 600/300 |
| 2012/0224664 A1* | 9/2012 | Maack ..................... A61B 6/02 378/7 |
| 2015/0053014 A1 | 2/2015 | Fetzer et al. |

* cited by examiner

Primary Examiner — Don K Wong
(74) Attorney, Agent, or Firm — Joseph F. Harding; The Small Patent Law Group LLC

(57) ABSTRACT

A measurement system is provided that includes a radiographic source, a detector, and at least one processor. The at least one processor is operably coupled to the detector and configured to: position the radiographic source in a first position relative to the object to image a first portion of the object, with the first position configured to maintain parallax for the first portion within a predetermined amount; obtain first imaging information of the first portion of the object in the first position; adjust the position of the radiographic source relative to the object to a second position, with the second position configured to maintain parallax for the second portion within a predetermined amount; obtain second imaging information of the second portion of the object in the second position; and generate an image of the object using the first imaging information and the second imaging information.

17 Claims, 5 Drawing Sheets

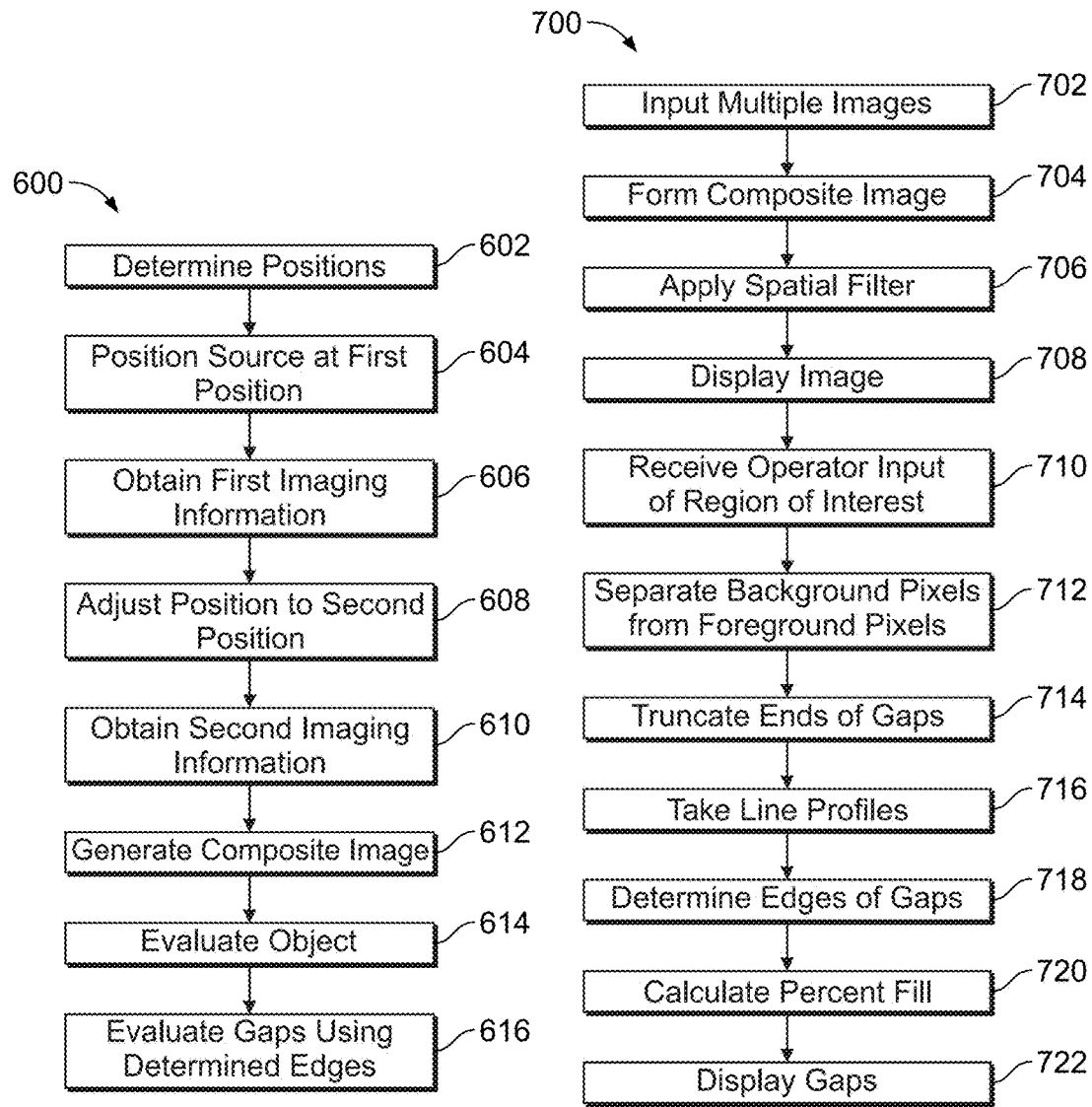

APPARATUSES AND METHODS FOR HIGH-PRECISION MEASUREMENT

FIELD OF EMBODIMENTS OF THE DISCLOSURE

Embodiments of the present disclosure generally relate to imaging and inspecting components, for example gaps between components that have been joined.

BACKGROUND OF THE DISCLOSURE

During a manufacturing process, two or more components may be joined together. The joint may be in a location that is difficult to visually inspect. For example, for an outer diameter of a tube that is swaged into a fitting, the joint may be on the interior of the fitting and not visible to the naked eye. Conventional approaches of inspecting such gaps may include cutting the piece in half to inspect the part. Such approaches require destruction of the part, and may not provide a desired accuracy, as the part may distort during the cutting process.

SUMMARY OF THE DISCLOSURE

Accordingly, improvement of inspecting objects is provided in various embodiments disclosed herein.

Certain embodiments of the present disclosure provide a measurement system that includes a radiographic source, a detector, and at least one processor. The radiographic source is movable between a plurality of positions. The detector is configured to be disposed opposite the radiographic source, with an object to be imaged disposed between the radiographic source and the detector. The at least one processor is operably coupled to the detector and configured to: position the radiographic source in a first position relative to the object to image a first portion of the object, with the first position configured to maintain parallax for the first portion within a predetermined amount; obtain first imaging information of the first portion of the object in the first position; adjust the position of the radiographic source relative to the object to a second position, with the second position configured to maintain parallax for the second portion within a predetermined amount; obtain second imaging information of the second portion of the object in the second position; and generate an image of the object using the first imaging information and the second imaging information.

Certain embodiments of the present disclosure provide a method. The method includes positioning a radiographic source in a first position relative to an object to image a first portion of the object. The first position is configured to maintain parallax for the first portion within a predetermined amount. The method also includes obtaining, with a detector, first imaging information of the first portion of the object in the first position. Also, the method includes adjusting the position of the radiographic source relative to the object to a second position. The second position is configured to maintain parallax for the second portion within a predetermined amount. Further, the method includes obtaining, with the detector, second imaging information of the second portion of the object in the second position. The method also includes generating an image of the object using the first imaging information and the second imaging information.

Certain embodiments of the present disclosure provide a tangible and non-transitory computer readable medium comprising one or more software modules. The software modules are configured to direct one or more processors to: position a radiographic source in a first position relative to an object to image a first portion of the object, the first position configured to maintain parallax for the first portion within a predetermined amount; obtain first imaging information of the first portion of the object in the first position; adjust the position of the radiographic source relative to the object to a second position, the second position configured to maintain parallax for the second portion within a predetermined amount; obtain second imaging information of the second portion of the object in the second position; and generate an image of the object using the first imaging information and the second imaging information.

BRIEF DESCRIPTION OF THE DRAWINGS

FIG. 6 provides a flowchart of a method according to an embodiment of the present disclosure.

FIG. 7 provides a flowchart of a method according to an embodiment of the present disclosure.

DETAILED DESCRIPTION OF THE DISCLOSURE

Figure 1:
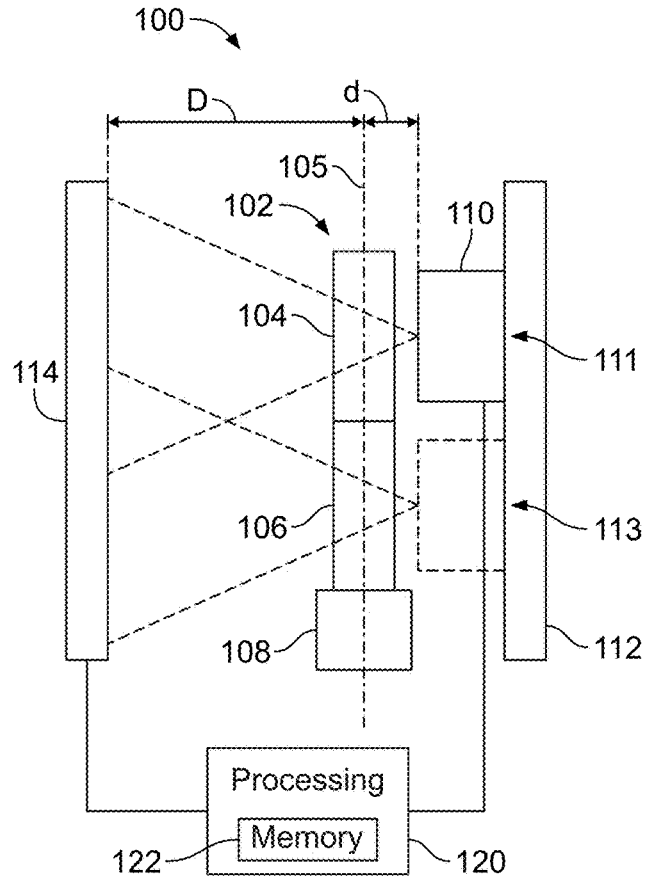
FIG. 1 provides a schematic view of a measurement system in accordance with various embodiments.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Embodiments of the present disclosure provide systems and methods for inspecting objects, for example objects featuring two components that have been joined. One example of such an object includes ferrules or fittings that have been swaged on to a tube. Various embodiments reduce parallax effects of imaging or maintain parallax within an acceptable level by limiting the angle of incidence for any given portion of an object by taking multiple images of the object from different locations or perspectives. Some embodiments provide for quick, non-destructive, reliable groove fill determination that may be applied to test parts or production parts to greatly reduce the risk of escapements, reduce costs, and/or inspect suspect parts.

To provide high enough resolution to support a desired level of precision, geometric magnification may be used. However, geometric magnification may increase the angle of incidence to the part being imaged, potentially leading to shadowing and blurring due to parallax. The parallax is addressed in various embodiments by taking multiple images with a re-positioning of an x-ray source and the object being imaged for each image. Then, the portions of each image with minimal parallax are spliced together to form a single image with low parallax. In some embodiments, the image may be spatially filtered to reduce the parallax effect on the measurement. Further, in some embodiments, an edge detection algorithm resistant to shadowing caused by parallax may be employed.

FIG. 1 provides a schematic view of a measurement system 100 in accordance with various embodiments. In the illustrated embodiment, the measurement system 100 includes a radiographic source 110, a detector 114, a fixture 108, and a processing unit 120. Generally, rays from the radiographic source 110 are transmitted through an object 102 to the detector 114, with imaging information collected by the detector 114 processed by the processing unit 120 to provide an image of the object 102. In the illustrated embodiment, the object 102 has a first portion 104 and a second portion 106. It may be noted that various embodiments may include additional components, or may not include all of the components shown in FIG. 1 (for example, various embodiments may provide sub-systems for use with other sub-systems to provide an imaging system). Further, it may be noted that certain aspects of the measurement system 100 shown as separate blocks in FIG. 1 may be incorporated into a single physical entity, and/or aspects shown as a single block in FIG. 1 (e.g., processing unit 120) may be shared or divided among two or more physical entities.

Figure 2:
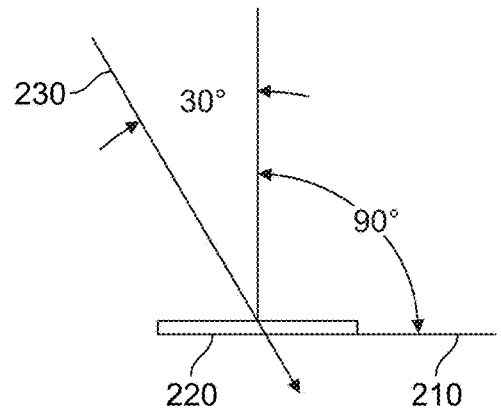
FIG. 2 illustrates a definition of how parallax may be measured.
Figure 3:
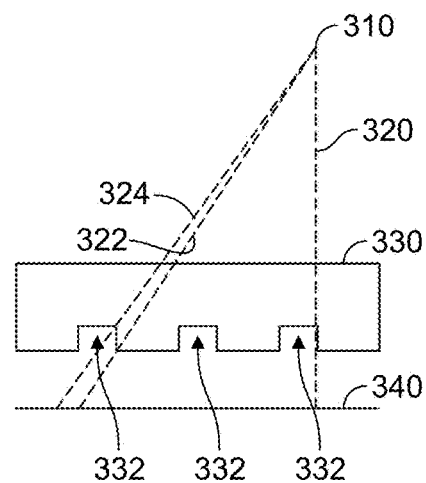
FIG. 3 illustrates an example of the effect of parallax.

It may be noted that, due to a distance from the object 102 to the detector 110, the image generated may be affected by a parallax effect of rays passing through the object 102 to the detector 114. FIGS. 2 and 3 illustrate examples of parallax and its effect. As seen in FIG. 2, parallax as used herein refers to the deviation from perpendicular between a transmitted ray (e.g., X-ray beam 230) toward a detector (e.g., detector 110) and a longitudinal axis 210 of an object 220 being imaged (e.g., a ferrule applied at the end of a shaft). The incidence angle in the illustrated example is 30 degrees. In the illustrated embodiment, the object 220 represents a tube and ferrule, and the cylindrical symmetry of the tube and ferrule reduces the effect of the transverse component to a small change in the tangent point of the beam to a groove between the ferrule and tube. The effect of the transverse component may be effectively negligible in various embodiments. Additionally, the groove may have a relatively small depth that represents a very small change in angle of the X-ray beam 230 that also acts to reduce the transverse component of parallax. Generally, the effect of parallax is to shift and blur features depending on their relative position in a field of view (FOV) as shown in FIG. 3, which illustrates blurring and shifting of an image due to non-perpendicular X-ray beams. In FIG. 3, an x-ray source 310 is treated as a point source to represent, for example, an x-ray source such as a nanofocus x-ray source having a small focal size. A first ray 320 passes through the object 330 (which has grooves 332) and is oriented generally perpendicular to the detector plane 340. However, second ray 322 and third ray 324 pass at an oblique angle through the object 330 and onto the detector plane 340, resulting in blurring and shifting of a resulting image.

Figure 4:
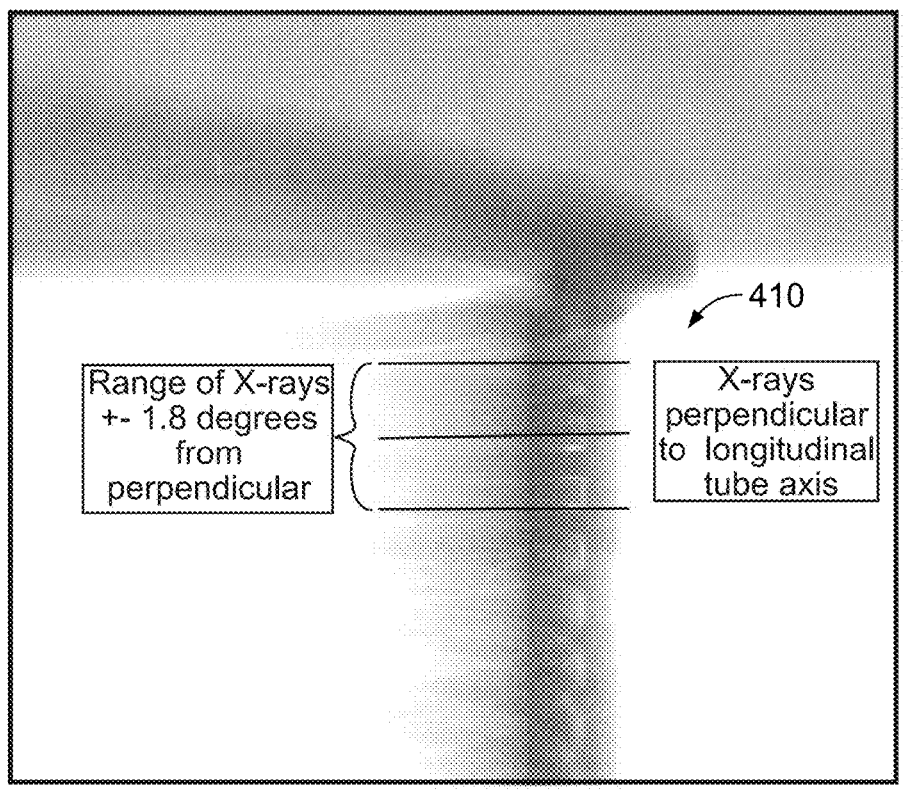
FIG. 4 depicts an example of a radiographic image in accordance with various embodiments.

In several example scenarios, images were generated using varying degrees of parallax and known gap or groove sizes to determine a maximum amount of parallax before measurement of gap size was affected (e.g., affected beyond a tolerable amount). For ferrules that had been swaged onto tubes, it was found that screening could be performed over a range of plus/minus 3.5 degrees of parallax. For the use of certain defect recognition software to analyze cross sections of ferrules and tubes, it was found that a limit of plus/minus 1.8 degrees of parallax existed. FIG. 4 illustrates an example digital radiograph of a machined specimen 410 to show the effect of parallax. It may be noted that the example of FIG. 4 was created using a level of geometric magnification (e.g., magnification resulting from the distances of the source and detector from the object being imaged) that may be higher than that used in practice for inspection of parts. It may be noted that the farther from perpendicular the incident X-ray beam becomes, the more the image of a gap or groove becomes blurred or distorted. It should be noted that the particular examples of FIGS. 2-4 are meant by way of example for illustrative purposes, and that other objects, ranges of parallax, or tolerable levels of parallax may be utilized in various embodiments.

Accordingly, with continued reference to FIG. 1, in various embodiments, the radiographic source 110 may be positioned selectively relatively to different portions of an object 102 being imaged to reduce the parallax effect and provide improved imaging and accuracy of measurement. For example, the processing unit 120 may be configured to determine two or more positions at which to image the object to maintain parallax effects at a desirable level or less for imaging within a desired tolerance.

Generally, the radiographic source 110 is configured to transmit electromagnetic rays to which the object 102 is at least partially transparent and/or translucent, allowing for the collection of rays by the detector 114. Based on the attenuation of the rays collected by the detector 114, an image may be reconstructed of the object 102. The radiographic source 110 may be an x-ray tube, for example. In some embodiments, the radiographic source 110 is a nanofocus x-ray tube having a very small focal point.

In the illustrated embodiment, the radiographic source 110 is movable between a plurality of positions. The radiographic source 110 may be continuously adjustable in various embodiments, and/or may be movable between discrete pre-set positions in other embodiments. In the illustrated example, the radiographic source is depicted in solid line at a first position 111 and in phantom line at a second position 113. The depicted system 100 includes a carriage 112 to which the detector 110 is operably coupled. The carriage 112 is controlled by the processing unit 120 in the illustrated embodiment to move the radiographic source 110 between the first position 111 and the second position 113. It may be noted that additional or alternative positions may be utilized in alternate embodiments. It may also be noted that the detector 114 may also be movable, for example, by being coupled to the same carriage as the radiographic source 110 or to a different carriage.

The radiographic source 110 is movable with respect to the object 102 to image the object 102 from different points. For example, at the first position 111, the source 110 provides a first field of view, and that the second position 113, the source 110 provides a second field of view. The particular locations of the positions may be selected to more effectively address parallax for the first portion 104 with the source 110 at the first position 111, and to more effectively address parallax for the second portion 106 with the source 110 at the second position 113. In the illustrated embodiment, the object 102 is secured in a stationary fixture 118 that does not move, with the radiographic source 110 configured to move. In other embodiments, the object 102 may be moved additionally or alternatively to movement by the source 110. Thus, the source 110 may move relative to the object 102 by movement of the source 110 while the object 102 is stationary, by movement of the object 102 while the source 110 is stationary, or by movement of both the object 102 and the source 110.

The detector 110 is coupled to the processing unit 120. The detector 110 receives rays from the source 110 and provides imaging information to the processing unit 120 that may be used to reconstruct an image. In the depicted embodiment, the detector 110 is disposed opposite the radiographic source 110, with the object 102 to be imaged disposed between the radiographic source 110 and the detector 114. Accordingly, rays passing through the object 102 from the source 110 are attenuated by the object 102 and received by the detector 114. It may be noted that in the illustrated embodiment, the radiographic source 110 is configured to be positioned more closely to the object 104 than is the detector 114 when imaging information is obtained. For example, as seen in FIG. 1, the radiographic source 110 is at a distance d from an axis 105 defined by the fixture 118 and object 104, and the detector is at a distance D from the axis 105.

The processing unit 120 is operably coupled to the detector 110 and the radiographic source 110. For example, the processing unit 120 may receive imaging information from the detector 110, and may provide control signals to the radiographic source 110 and/or to the carriage 112. The processing unit 120 may include processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may distributed among various units or housings. Generally, various aspects of the processing unit 120 act individually or cooperatively to perform one or more aspects of the methods, steps, or processes discussed herein. Instructions to perform one or more aspects of the methods, steps, or processes discussed herein may be stored on the memory 122, which may include a tangible, non-transitory computer readable medium on which the instructions are saved.

In the illustrated embodiment, the processing unit 120 is configured (e.g., programmed) to position the radiographic source 110 in a first position 111 relative to the object 102 to image the first portion 104 of the object 102. The first position 111 is configured to maintain parallax for the first portion 104 within a predetermined amount. The predetermined amount may be expressed as a number (e.g., a value defining a range of angles of parallax), a percentage corresponding to a size of an aspect of the object to be imaged. The first position 111 may be selected to minimize parallax for a given feature (e.g., a gap or groove) of the first portion 104 as one example, or, as another example, may be selected to limit parallax within a defined level for a number of features or aspects of the first portion 104. Both the particular locations of the positions as well as the number of positions to be employed may be selected, for example, based on maintaining parallax within a desired limit, and may be selected using the geometrical configuration of the object 104 being imaged as well as the measurement system 100. For example, to determine the positions (e.g., the first position 111, the second position 113, and/or any other additional or alternative positions), one or more of the following may be considered: the distance from the source 110 to the object 102 and/or the detector 114, the distance from the detector 114 to the source 110 and/or to the object 102, the location of one or more features (e.g., gaps or grooves) of the object 102 to be inspected, the size of the one or more features, and the required precision of a measurement using a generated image. It may be noted that additional or alternative features may be inspected or analyzed in various embodiments. For example, in some embodiments, high precision measurements for casting defects such as pores, gas holes, cracks, shrinkage, and/or inclusions may be performed In some embodiments, the first position 111 may be selected such that rays from the radiographic source 110 impact the center of the first portion 104 perpendicularly in the first position 111, and the second position 113 may be selected such that rays from the radiographic source 110 impact the center of the second portion perpendicularly in the second position 113.

With the radiographic source 110 in the first position 111, the processing unit 120 next obtains first imaging information of the first portion 104 of the object 102 in the first position 111. For example, the processing unit 120 may control the radiographic source 110 to produce x-rays, and receive information from the detector 114 corresponding to rays passing through the first portion 104 of the object 102.

Next, the processing unit 120 of the illustrated example adjusts the position of the radiographic source 110 relative to the object 102 to the second position 113 (e.g., by sending control signals to the carriage 112 to move the processing unit 120 a desired amount relative to the object 102). Generally similar to the first position 111 in various respects, the second position 113 is configured to maintain parallax for the second portion 106 within a predetermined amount. The second position 113 may be selected to minimize parallax for a given feature (e.g., a gap or groove) of the second portion 106 as one example, or, as another example, may be selected to limit parallax within a defined level for a number of features or aspects of the second portion 106.

With the radiographic source 110 in the second position 113, the processing unit 120 next obtains second imaging information of the second portion 106 of the object 102 in the second position 113. For example, the processing unit 120 may control the radiographic source 110 to produce x-rays, and receive information from the detector 114 corresponding to rays passing through the second portion 106 of the object 102.

After obtaining the first and second imaging information, the processing unit 120 generates an image of the object 102 using the first imaging information and the second imaging information. For example, the processing unit 120 may generate a first image using the first imaging information and a second image using the second imaging information. Parallax of the first portion 104 is within an acceptable limit in the first image as discussed herein, and parallax of the second portion 106 is within an acceptable limit in the second image. The first and second images may be joined, for example, at a splice point corresponding to a location at or near a border of the first and second portions. For example, a predetermined reference point may be selected to define the splice point based on the geometry of the object 102. In some embodiments, for example, the object 102 may include a series of gaps or grooves that are desired to be inspected, and the first and second positions may be selected to provide the splice point at a location that does not coincide with any of the gaps or grooves.

Figure 5:
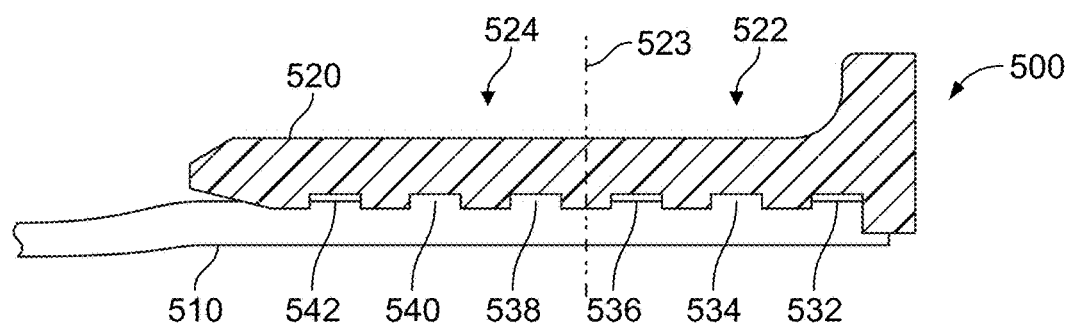
FIG. 5 illustrates an example object to be imaged and inspected in accordance with various embodiments.

It may be noted that, in some embodiments, the object 102 includes at least one gap, and the processing unit 120 is configured to determine a fill level of the at least one gap using the image generated using information from plural positions of the radiographic source 110. In some embodiments, the object 102 includes a first plurality of gaps in the first portion 104 and a second plurality of gaps in the second portion 106. FIG. 5 depicts an example object 500 that may be inspected using a measurement system (e.g., measurement system 100) in accordance with various embodiments. In the example of FIG. 5, the object 500 includes a ferrule 520 that has been swaged to a tube 510, with the tube 510 swaged into grooves of the ferrule 520. In the illustrated embodiment, the tube 510 and the ferrule 520 define a series of gaps, including a first gap 532, a second gap 534, a third gap 536, a fourth gap 538, a fifth gap 540, and a sixth gap 542. Border 523 depicts the division between the first portion 522 (which may be imaged with a radiographic source in a first position) and the second portion 524 (which may be imaged with a radiographic source in a second position). As seen in FIG. 5, the first gap 532, second gap 534, and third gap 536 are located in the first portion 522, and the fourth gap 538, fifth gap 540, and sixth gap 542 are located in the second portion 524. The border 523, which does not pass through a gap, may correspond to a splice point used to join first and second images of the first portion 522 and the second portion 524, respectively. In some embodiments, the length of the ferrule 520 may be between 0.5 and 1 inch, and the diameter of the tube between 0.375 and 5.5 inches.

A percentage fill of gaps defined by the tube 510 and the ferrule 520 formed during a swaging process may be determined using an image generated as discussed herein, for example to assure strength in a tightness of a joint between the ferrule 520 and the tube 510, for example to help assure fluid or gas tightness in the fit. In some embodiments, the first gap 532 may be inspected to assure at least 50 percent fill, and the remaining gaps inspected to assure at least 70 percent fill. For example, one or more processors (e.g., processing unit 120) may be configured to determine a fill level of the gaps. In some embodiments, the one or more processors are configured to determine edges of gaps by applying a threshold to line profiles of the image, and to determine the fill level using the determined edges of gaps. (See also, e.g., FIGS. 6 and 7 and related discussion.)

FIG. 6 provides a flowchart of a method 600 for imaging an object, in accordance with various embodiments. The method 600, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 600 may be able to be used as one or more algorithms to direct hardware (e.g., portions, aspects, and/or variations of the method may be implemented by one or more aspects of the processing unit 120 using instructions stored on the memory 122) to perform one or more operations described herein.

At 602, positions at which a radiographic source (e.g., radiographic source 110) will be positioned with respect to an object (e.g., object 102) for acquiring imaging information are determined. Generally, the positions are selected or determined to provide a series of images, with each image having an amount of parallax at or below a predetermined tolerable level for a corresponding portion of the object. The number and location of the positions may be determined, for example, based on the geometry of the object being imaged (e.g., one or more features such as gaps of the object) and/or the system collecting the imaging information. The images for each position may then be joined to form a composite image. The positions may also be selected or determined to avoid placement of a splice point between image portions on a feature of interest, such as a gap or groove.

At 604, the radiographic source is positioned at a first position relative to the object to be imaged to image a first portion of the object. The first position is configured to maintain parallax for a first portion of the object within a predetermined amount.

At 606, first imaging information is obtained. The first imaging information is obtained for the first portion of the object, with the source in the first position. The first imaging information may be reconstructed into a first image that will be joined with one or more other images to form a composite image.

At 608, the position of the radiographic source is adjusted relative to the object to a second position. The second position is configured to maintain parallax for a second portion of the object with a predetermined amount.

At 610, second imaging information is obtained. The second imaging information is obtained for the second portion of the object, with the source in the second position. The second imaging information may be reconstructed into a second image that will be joined with one or more other images, including the first image, to form a composite image. It may be noted that while two positions and corresponding object portions are discussed in connection with the illustrated example, additional positions and corresponding portions may be utilized in other embodiments.

At 612, the first and second imaging information (e.g., first and second images corresponding to respective first and second portions of the object being imaged) are combined to generate an image (e.g., a composite image) of the object. The first and second imaging information (e.g., first and second images) may be joined at a predetermined splice point corresponding to a location within a field of view of the source at each position. In embodiments where more than two positions are utilized, more than two images may be joined to generate the image of the object. By using individual images minimizing or reducing parallax for corresponding portions of the object, a composite image having reduced parallax effect (e.g., relative to an image formed from a single acquisition of imaging information from a single position) may be provided.

At 614, the object being imaged is evaluated for satisfaction of a target. For example, the object may be evaluated to determine if the object satisfies one or more quality control standards. As one example, the object may include a series of gaps, and the gaps may be evaluated to see if the gaps satisfy a minimum predetermined fill level or percentage fill. In the illustrated embodiment, at 616, edges of gaps are determined, and the fill level is determined by using the determined edges of the gaps. The edges of the gaps may be determined for example, applying a threshold to line profiles of the image. Additional discussion regarding one example method for determining gap fill level of an object is discussed in connection with FIG. 7.

FIG. 7 provides a flowchart of a method 700 for imaging an object, in accordance with various embodiments. The method 700, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 700 may be able to be used as one or more algorithms to direct hardware (e.g., portions, aspects, and/or variations of the method may be implemented by one or more aspects of the processing unit 120 using instructions stored on the memory 122) to perform one or more operations described herein.

At 702, multiple images of a single part are input. Each image, for example, may be acquired as discussed herein to maintain parallax within each image within a desired level. At 704, a composite image is formed from the multiple images. Each image may be joined to one or more neighboring images at a predetermined splice point. By joining individual images, each of which has limited parallax for a given portion of an object, a composite image having limited parallax for the entire object may be generated.

At 706, a spatial filter is applied. For example, a spatial filter may be applied in a direction parallel to a measurement direction (e.g., along the length of a ferrule that has been swaged to a tube). In some embodiments, the spatial applying the spatial filter includes taking the first derivative of a signal with respect to position parallel to the direction of measurement.

At 708, the resulting image (e.g., the composite image to which the spatial filter has been applied) is displayed to an operator. At 710, the operator inputs a region of interest. For example, the operator may identify one or more gaps for which a fill level or percentage is to be determined. At 712, background pixels are separated from foreground pixels. For example, Otsu's Method may be employed to sort gap pixels (e.g., pixels corresponding to one or more gaps selected by an operator) from non-gap pixels.

It may be noted that only a central portion of a gap may be examined in some embodiments to determine compliance with a quality control standard. Accordingly, in the illustrated embodiment, ends of gaps are truncated at 714. Truncating the ends of the gaps to evaluate only a central portion may further reduce the effect of parallax in various embodiments. At 716, line profiles parallel to the direction of measurement are taken of the image (or portions thereof) provided at 706 (e.g., line profiles are taken of the truncated portions of the selected gaps).

At 718, edges of gaps (e.g., edges of gaps between two joined parts, such as edges corresponding to edges of a tube and corresponding portions of a ferrule to which the tube has been swaged) are determined. For example, a threshold may be applied to the line profiles generated at 716. As one example, a change of 90% or more in signal strength may be considered to satisfy a threshold indicating the presence of an edge. At 720, a percent fill is calculated for each gap or groove. For example, the percentage of the gap between a ferrule and a tube relative to the depth of a groove into which the ferrule extends may be determined.

At 722, the gaps are displayed to an operator. At 724, the operator links discontinuous sections that should be treated as a single gap. At 726, a report is output showing percentage gap fill for each groove. Alternatively or additionally, a pass/fail determination for each groove and/or for the object as a whole based on a predetermined minimum fill level or percentage fill is reported. It may be noted that additional or alternative features may be displayed and analyzed in various embodiments. For example, in some embodiments, high precision measurements for casting defects such as pores, gas holes, cracks, shrinkage, and/or inclusions may be performed.

Figure 8:
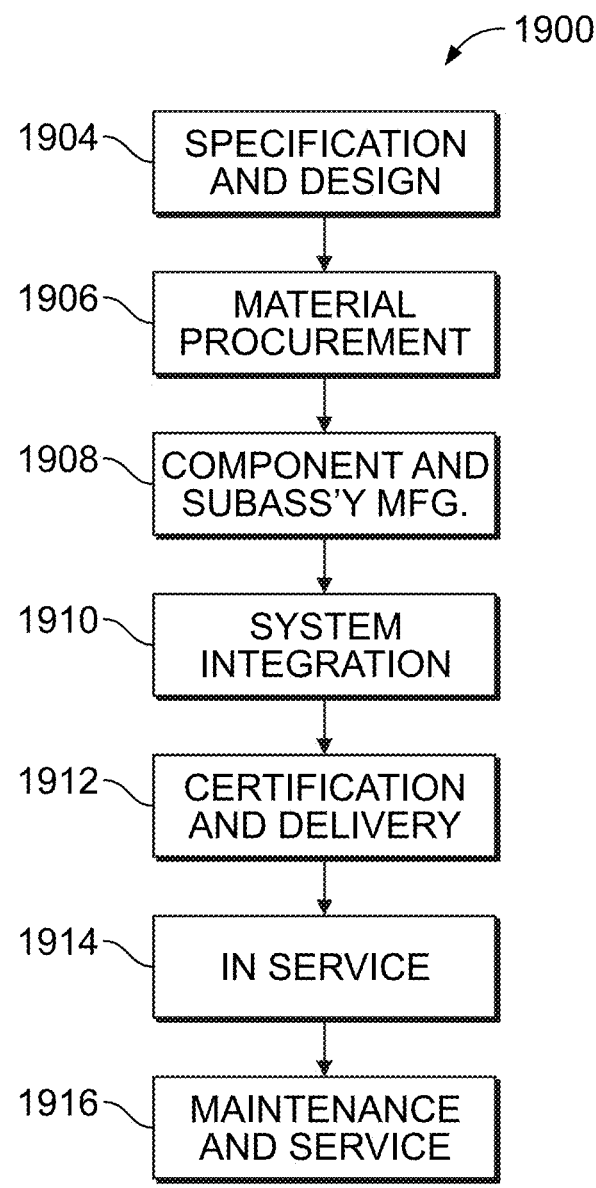
FIG. 8 is a block diagram of aircraft production and service methodology.
Figure 9:
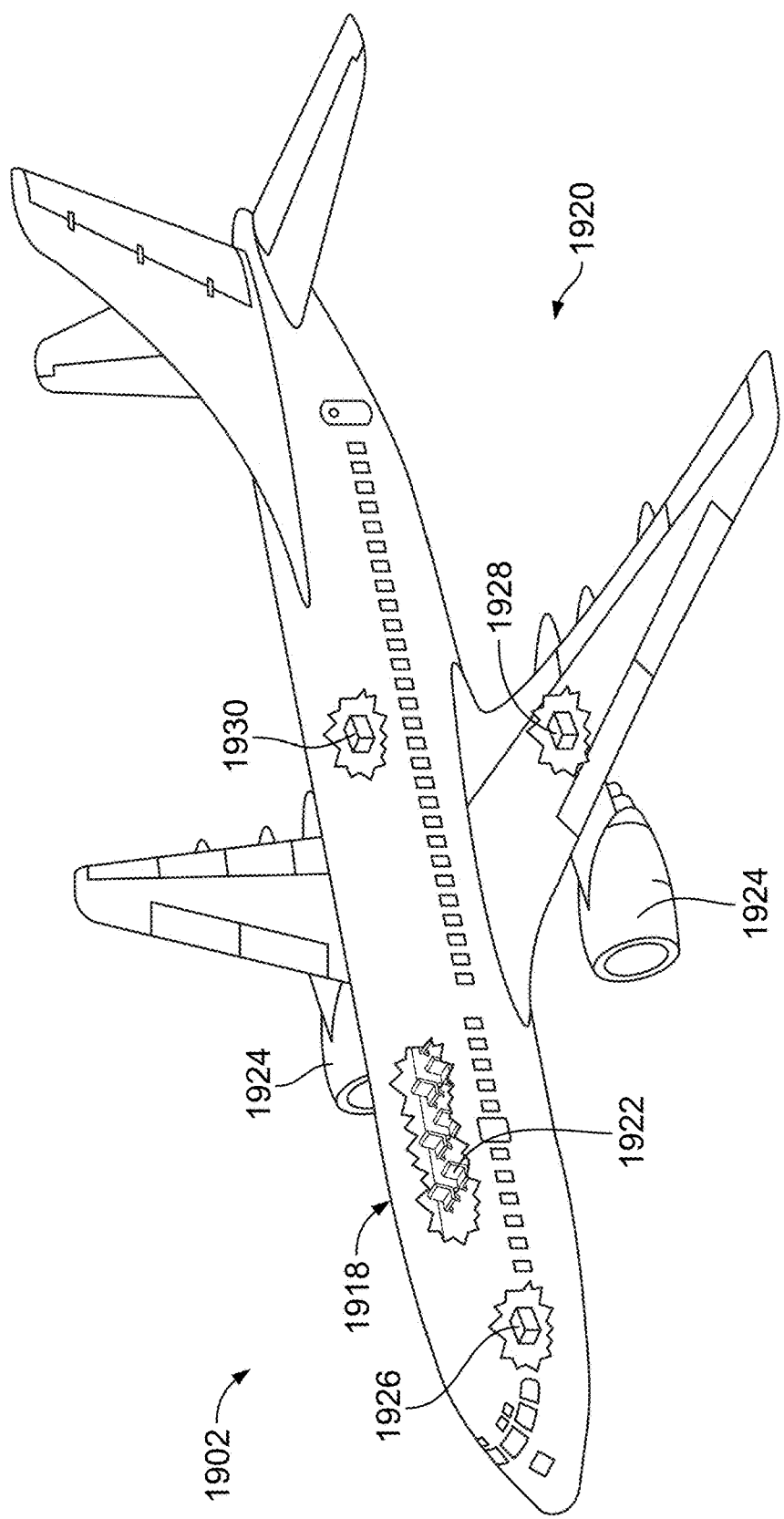
FIG. 9 is a schematic illustration of an aircraft.

Examples of the present disclosure may be described in the context of aircraft manufacturing and service method 1900 as shown in FIG. 8 and aircraft 1902 as shown in FIG. 9. During pre-production, illustrative method 1900 may include specification and design (block 1904) of aircraft 1902 and material procurement (block 1906). During production, component and subassembly manufacturing (block 1908) and system integration (block 1910) of aircraft 1902 may take place. Thereafter, aircraft 1902 may go through certification and delivery (block 1912) to be placed in service (block 1914). While in service, aircraft 1902 may be scheduled for routine maintenance and service (block 1916). Routine maintenance and service may include modification, reconfiguration, refurbishment, etc. of one or more systems of aircraft 1902. For example, in various embodiments, examples of the present disclosure may be used in conjunction with one or more of blocks 1908 or 1916.

Each of the processes of illustrative method 1900 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

As shown in FIG. 9, aircraft 1902 produced by illustrative method 1900 may include airframe 1918 with a plurality of high-level systems 1920 and interior 1922. Examples of high-level systems 1920 include one or more of propulsion system 1924, electrical system 1926, hydraulic system 1928, and environmental system 1930. Any number of other systems may be included. Although an aerospace example is shown, the principles disclosed herein may be applied to other industries, such as the automotive industry. Accordingly, in addition to aircraft 1902, the principles disclosed herein may apply to other vehicles, e.g., land vehicles, marine vehicles, space vehicles, etc. In various embodiments, examples of the present disclosure may be used in conjunction with airframe 1918.

Apparatus(es) and method(s) shown or described herein may be employed during any one or more of the stages of the manufacturing and service method 1900. For example, components or subassemblies corresponding to component and subassembly manufacturing 1908 may be fabricated or manufactured in a manner similar to components or subassemblies produced while aircraft 1902 is in service. Also, one or more examples of the apparatus(es), method(s), or combination thereof may be utilized during production stages 1908 and 1910, for example, by substantially expediting assembly of or reducing the cost of aircraft 1902. Similarly, one or more examples of the apparatus or method realizations, or a combination thereof, may be utilized, for example and without limitation, while aircraft 1902 is in service, e.g., maintenance and service stage (block 1916).

Different examples of the apparatus(es) and method(s) disclosed herein include a variety of components, features, and functionalities. It should be understood that the various examples of the apparatus(es) and method(s) disclosed herein may include any of the components, features, and functionalities of any of the other examples of the apparatus(es) and method(s) disclosed herein in any combination, and all of such possibilities are intended to be within the spirit and scope of the present disclosure.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a processor or a processing unit includes processing circuitry configured to perform one or more tasks, functions, or steps, such as those described herein. For instance, the processor may be a logic-based device that performs operations based on instructions stored on a tangible and non-transitory computer readable medium, such as memory. It may be noted that a "processor," as used herein, is not intended to necessarily be limited to a single processor or single logic-based device. For example, the processor may include a single processor (e.g., having one or more cores), multiple discrete processors, one or more application specific integrated circuits (ASICs), and/or one or more field programmable gate arrays (FPGAs). In some embodiments, the processor is an off-the-shelf device that is appropriately programmed or instructed to perform operations, such as the algorithms described herein.

The processor may also be a hard-wired device (e.g., electronic circuitry) that performs the operations based on hard-wired logic that is configured to perform the algorithms described herein. Accordingly, the processor may include one or more ASICs and/or FPGAs. Alternatively or in addition to the above, the processor may include or may be associated with a tangible and non-transitory memory having stored thereon instructions configured to direct the processor to perform the algorithms described herein.

It is noted that operations performed by the processor (e.g., operations corresponding to the methods/algorithms described herein, or aspects thereof) may be sufficiently complex that the operations may not be performed by a human being within a reasonable time period based on the intended application of the assay system. The processor may be configured to receive signals from the various subsystems and devices of the system or user inputs from the user. The processor may be configured to perform the methods described herein.

Processors may include or be communicatively coupled to memory. In some embodiments, the memory may include non-volatile memory. For example, the memory may be or include read-only memory (ROM), random-access memory (RAM), electrically erasable programmable read-only memory (EEPROM), flash memory, and the like. The memory may be configured to store data regarding operating parameters of the system 100.

In an exemplary embodiment, the processor executes a set of instructions that are stored in one or more storage elements, memories, and the like. Embodiments include non-transitory computer-readable media that include set of instructions for performing or executing one or more processes set forth herein. Non-transitory computer readable media may include all computer-readable media, except for transitory propagating signals per se. The non-transitory computer readable media may include generally any tangible computer-readable medium including, for example, persistent memory such as magnetic and/or optical disks, ROM, and PROM and volatile memory such as RAM. The computer-readable medium may store instructions for execution by one or more processors.

The set of instructions may include various commands that instruct the system to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A measurement system comprising:
   a radiographic source, the radiographic source movable between a plurality of positions;
   a detector configured to be disposed opposite the radiographic source, wherein an object to be imaged is disposed between the radiographic source and the detector; and
   at least one processor, the at least one processor operably coupled to the detector and configured to:
     determine a first position for the radiographic source relative to the object for imaging a first portion of the object based on at least one of a gap or a groove located in the first portion of the object, the first position configured to maintain a deviation from perpendicular between a transmitted ray from the radiographic source in the first position toward the detector and a longitudinal axis of the object within a predetermined amount for at least a portion of the first portion of the object;
     determine a second position for the radiographic source relative to the object for imaging a second portion of the object based on at least one of a gap or a groove located in the second portion of the object, the second position configured to maintain a deviation from perpendicular between a transmitted ray from the radiographic source in the second position toward the detector and a longitudinal axis of the object within a predetermined amount for at least a portion of the second portion of the object;
     position the radiographic source in the first position relative to the object to image the first portion of the object;
     obtain first imaging information of the first portion of the object in the first position;
     adjust the position of the radiographic source relative to the object to the second position to image the second portion of the object;
     obtain second imaging information of the second portion of the object in the second position; and
     generate an image of the object using the first imaging information and the second imaging information.

2. The measurement system of claim 1, wherein the object comprises at least one gap, wherein the at least one processor is configured to determine a fill level of the at least one gap using the image.

3. The measurement system of claim 2, wherein the object comprises a first plurality of gaps in the first portion and a second plurality of gaps in the second portion.

4. The measurement system of claim 3, wherein the at least one processor is configured to determine edges of gaps by applying a threshold to line profiles of the image, and to determine the fill level using the determined edges of gaps.

5. The measurement system of claim 3, wherein the at least one processing unit is configured to combine the first and second imaging information at a splice point, and to determine the first and second positions such that the splice point does not coincide with a gap location.

6. The measurement system of claim 3, wherein the object includes a first component that has been swaged onto a second component.

7. The measurement system of claim 1, wherein the radiographic source and detector are positioned to provide geometric magnification of the object.

8. A method comprising:
   determining a first position for a radiographic source relative to an object for imaging a first portion of the object based on at least one of a gap or a groove located in the second portion of the object, the first position configured to maintain a deviation from perpendicular between a transmitted ray from the radiographic source in the first position toward the detector and a longitudinal axis of the object within a predetermined amount for at least a portion of the first portion of the object;
   determining a second position for the radiographic source relative to the object for imaging a second portion of the object based on at least one of a gap or a groove located in the second portion of the object, the second position configured to maintain a deviation from perpendicular between a transmitted ray from the radiographic source in the second position toward the detector and a longitudinal axis of the object within a predetermined amount for at least a portion of the second portion of the object;
   positioning the radiographic source in the first position relative to the object to image the first portion of the object;
   obtaining, with a detector, first imaging information of the first portion of the object in the first position;
   adjusting the position of the radiographic source relative to the object to the second position to image the second portion of the object;
   obtaining, with the detector, second imaging information of the second portion of the object in the second position; and
   generating an image of the object using the first imaging information and the second imaging information.

9. The method of claim 8, wherein the object comprises at least one gap, the method comprising determining a fill level of the at least one gap using the image.

10. The method of claim 9, wherein the object comprises a first plurality of gaps in the first portion and a second plurality of gaps in the second portion.

11. The method of claim 10, further comprising determining edges of gaps by applying a threshold to line profiles of the image, and determining the fill level using the determined edges of gaps.

12. The method of claim 10, further comprising combining the first and second imaging information at a splice point, wherein the first and second positions are configured such that the splice point does not coincide with a gap location.

13. The measurement system of claim 10, wherein the object includes a first component that has been swaged onto a second component.

14. The method of claim 8, wherein the radiographic source and detector are positioned to provide geometric magnification of the object.

15. A tangible and non-transitory computer readable medium comprising one or more software modules configured to direct one or more processors to:
   determine a first position for a radiographic source relative to an object for imaging a first portion of the object based on at least one of a gap or a groove located in the first portion of the object, the first position configured to maintain a deviation from perpendicular between a transmitted ray from the radiographic source in the first position toward the detector and a longitudinal axis of the object within a predetermined amount for at least a portion of the first portion of the object;
   determine a second position for the radiographic source relative to the object for imaging a second portion of the object based on at least one of a gap or a groove located in the second portion of the object, the second position configured to maintain a deviation from perpendicular between a transmitted ray from the radiographic source in the second position toward the detector and a longitudinal axis of the object within a predetermined amount for at least a portion of the second portion of the object
   position the radiographic source in the first position relative to the object to image the first portion of the object;
   obtain first imaging information of the first portion of the object in the first position;
   adjust the position of the radiographic source relative to the object to the second position to image the second portion of the object;
   obtain second imaging information of the second portion of the object in the second position; and
   generate an image of the object using the first imaging information and the second imaging information.

16. The tangible and non-transitory computer readable medium of claim 15, wherein the object comprises at least one gap, wherein the one or more software modules are further configured to direct the one or more processors to determine a fill level of the at least one gap using the image.

17. The tangible and non-transitory computer readable medium of claim 16, wherein the one or more software modules are further configured to direct the one or more processors to combine the first and second imaging information at a splice point, wherein the first and second positions are configured such that the splice point does not coincide with a gap location.

* * * * *